(12) United States Patent  
Weyl

(10) Patent No.: US 6,206,377 B1
(45) Date of Patent: Mar. 27, 2001

(54) SEAL ARRANGEMENT FOR A SENSING ELEMENT OF A GAS SENSOR

(75) Inventor: Helmut Weyl, Schwieberdingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/283,836

(22) Filed: Mar. 31, 1999

(30) Foreign Application Priority Data

Apr. 1, 1998 (DE) .............................. 198 14 503

(51) Int. Cl.[7] .............................. F16J 15/00; G01N 27/26
(52) U.S. Cl. .............................. 277/317; 277/654; 277/943; 204/424; 204/431
(58) Field of Search .............................. 277/317, 637, 277/654, 534, 542, 650, 943; 204/424, 428, 431, 432

(56) References Cited

U.S. PATENT DOCUMENTS

| | | | |
|---|---|---|---|
| 3,960,692 | * 6/1976 | Weyl et al. | 204/195 S |
| 4,019,974 | * 4/1977 | Weyl et al. | 204/195 S |
| 4,145,272 | * 3/1979 | Nakamura et al. | 204/195 S |
| 4,283,261 | * 8/1981 | Maurer et al. | 204/195 S |
| 4,324,632 | * 4/1982 | Tantram et al. | 204/195 P |
| 4,474,648 | * 10/1984 | Tantram et al. | 204/1 T |
| 4,478,067 | * 10/1984 | Ohta et al. | 73/23 |
| 4,810,352 | * 3/1989 | Bone et al. | 204/432 |
| 4,818,363 | * 4/1989 | Bayha et al. | 204/426 |
| 5,228,975 | * 7/1993 | Yamada et al. | 204/424 |
| 5,795,454 | * 8/1998 | Friese et al. | 204/424 |
| 5,942,092 | * 8/1999 | Weyl et al. | 204/424 |
| 5,949,023 | * 9/1999 | Weyl | 174/77 R |
| 6,083,371 | * 7/2000 | Weyl et al. | 204/426 |

FOREIGN PATENT DOCUMENTS 195 32 090   3/1997 (DE) .
94/29710 * 12/1994 (WO) .

* cited by examiner

*Primary Examiner*—Anthony Knight
*Assistant Examiner*—Alison K. Pickard
(74) *Attorney, Agent, or Firm*—Kenyon & Kenyon

(57) ABSTRACT

A seal arrangement for a sensing element of a gas sensor, in particular for determining the oxygen content in exhaust gases of internal combustion engines, includes a packet made up of several seal elements, packed one on top of another, which immobilize the sensing element in a longitudinal bore of a metallic probe housing. A funnel-shaped diversion element lying in the axial direction of the sensor is integrated into the seal elements packed one above another in such a way that gas permeability between the diversion element and the inner wall of the probe housing is ensured. Toward the measured-gas end of the sensor, a small gap remains open between the sensing element and the diversion element.

11 Claims, 1 Drawing Sheet

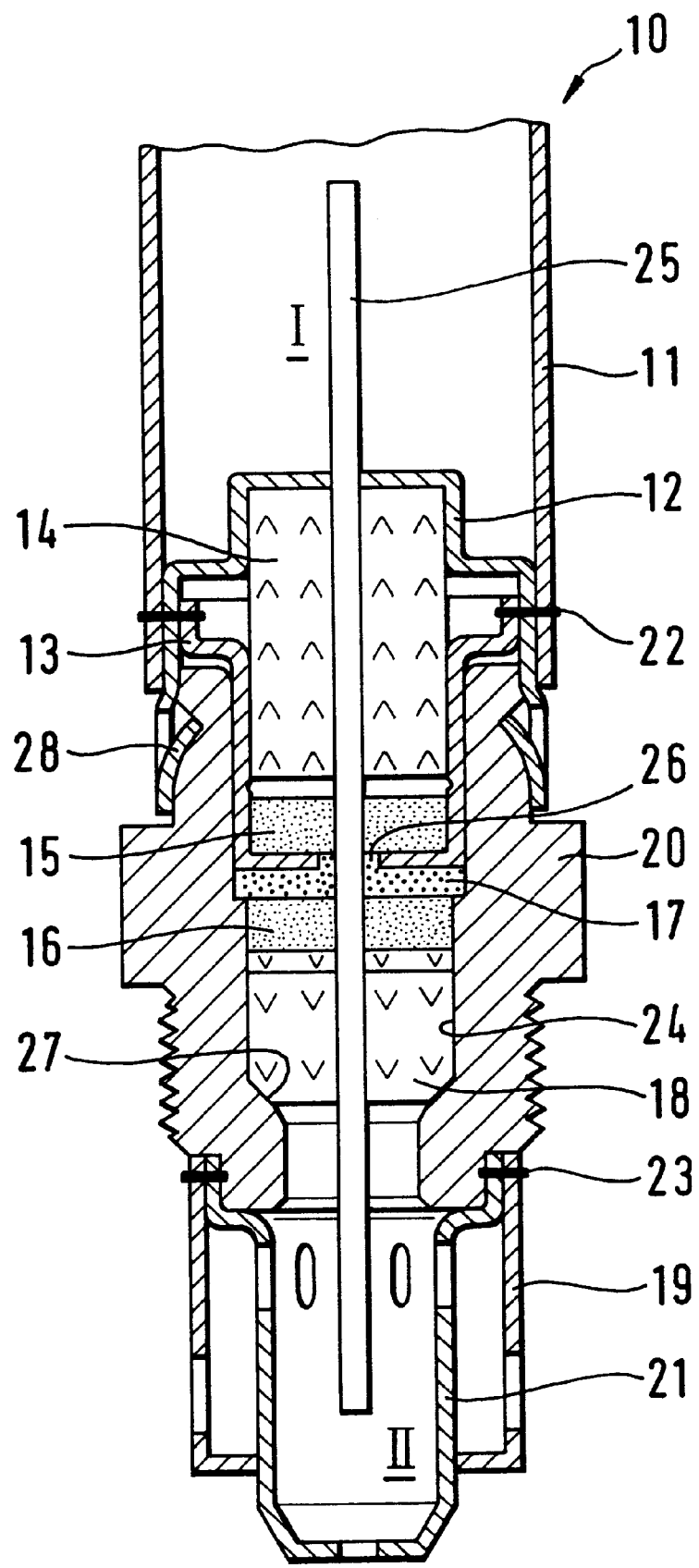

SEAL ARRANGEMENT FOR A SENSING ELEMENT OF A GAS SENSOR

FIELD OF THE INVENTION

The present invention relates to a seal arrangement for a sensing element of a gas sensor, in particular for determining the oxygen content in exhaust gases of internal combustion engines, this seal arrangement comprising a packet made up of several seal elements, packed one on top of another, which immobilize the sensing element in a longitudinal bore of a metallic probe housing.

BACKGROUND INFORMATION

What usually serves as the seal arrangement for a sensing element of oxygen probes is a precompressed and presintered powder packing made of steatite, which during assembly is exposed to a high axial pressure and is thereby reshaped. The sealing effect of this principle with respect to exhaust gases is entirely sufficient, but fuel in liquid or vapor form, and water vapor, can diffuse through the seal element and thereby interfere with probe operation.

German Patent No. 195 32 090 describes a seal arrangement which improves the seal effect with respect to fuel vapor by using a so-called "sandwich packing" of seal elements, in which a boron nitride disk placed in the packing decreases permeability for hydrocarbons. This solution is expensive due to the use of boron nitride.

A further alternative would be fusible sealing of the sensing element. The development of this approach requires extremely precise matching of the coefficients of thermal expansion of the materials used, which can lead to problems in large-volume production.

SUMMARY OF THE INVENTION

It is therefore an object of the present invention to provide a seal arrangement for a sensing element of a gas sensor, in particular an oxygen sensor for determining the oxygen content in exhaust gases of internal combustion engines, in such a way that a substantial improvement in resistance to gasoline vapor and water vapor, and a decrease in cost as compared to the "sandwich" approach using a boron nitride disk, are achieved.

According to the present invention, the above object is achieved, in a seal arrangement, in that a funnel-shaped diversion element lying in the axial direction of the sensor is integrated into the seal elements packed one above another in such a way that gas permeability between the diversion element and the inner wall of the probe housing is ensured, and that toward the measured-gas end of the sensor, a small gap remains open between the sensing element and the diversion element.

The effectiveness of the funnel-shaped diversion element lies in the fact that the hydrocarbons and water vapor diffusing from the exhaust gas side through a lower dense powder packing encounter the lower end surface of the diversion funnel, and there can for the most part escape into the atmosphere through the small gap formed between the sensing element and the funnel-shaped diversion element and also through a space between the inner protective sleeve and the outer wall of the probe housing. To ensure that the gases cannot get into the reference air space of the probe, the metallic funnel-shaped diversion element as well as the inner and outer protective sleeves must be joined to one another via a sealed full-circumference laser weld seam.

The effectiveness of the funnel-shaped diversion element can be increased by the fact that placed before its outer end face on the measured-gas side is a coarsely porous powder packing, for example made of steatite that has been presintered at temperatures of 750°, whose diffusion resistance is much lower with respect to the dense powder packing adjoining it toward the measured-gas side and with respect to the dense powder packing adjoining it on the connection side.

It is also alternatively possible to use, instead of the coarsely porous powder packing, a ceramic disk having transverse holes or ventilation grooves extending radially on the end face, with which the same effect as with the coarsely porous powder packing can be achieved.

In summary, the advantages of the seal arrangement according to the present invention are as follows:

- a substantial improvement in resistance to gasoline vapor and water vapor as compared to the approach commonly used today;
- a decrease in cost as compared to the "sandwich" approach using a boron nitride disk;
- the fact that despite the additional funnel-shaped diversion element, the number of components is no greater than with the "sandwich" approach; and
- the fact that as compared with the fusible glass sealing approach, no new and (in some cases) critical process steps are required.

BRIEF DESCRIPTION OF THE DRAWING

The FIGURE shows a gas sensor having the seal arrangement according to the present invention.

DETAILED DESCRIPTION

The FIGURE shows a gas sensor 10, for example an electrochemical oxygen sensor, which has within a metal probe housing 20, which serves as mounting means for installation in a measured-gas tube (not depicted), an elongated, plate-shaped sensing element 25. The end at the top of the FIGURE will be referred to hereinafter as the connection end 1, and the lower end as the measured-gas end 11.

Sensing element 25 is surrounded toward connection end I by an inner protective sleeve 12 and an outer protective sleeve 11. Measured-gas end II of sensing element 25 projects out of probe housing 20, and is surrounded by an inner protective tube 21 and an outer protective tube 19. Inner and outer protective tubes 21 and 19 are fastened to probe housing 20 by a weld 23, and have inlet and outlet openings for the gas to be measured. Resting on a shoulder-shaped annular surface 27 of longitudinal bore 24 of probe housing 20 is a lower or measured-gas-side ceramic insulator 18 which has a continuous orifice, running in the axial direction of longitudinal bore 24 of probe housing 20, through which sensing element 25 projects. Also arranged inside longitudinal bore 24 of probe housing 20, spaced away from measured-gas-side ceramic insulator 18, is a connection-side upper ceramic insulator 14 which also has a central, continuous, connection-side orifice in the direction of longitudinal bore 24 of probe housing 20. The latter orifice is aligned with the orifice of the lower, measured-gas-side ceramic insulator 18. Upper ceramic insulator 14 is also closed off at the end by inner protective sleeve 12.

Lying between measured-gas ceramic insulator 18 and connection-side ceramic insulator 14 are, in this order, a lower dense powder packing 16, a coarsely porous powder packing 17, the end of a funnel-shaped diversion element 13, and an upper dense powder packing 15. Seal elements 15, 17, 16 form a seal packing, with the end face of funnel-shaped diversion element 13 interposed. Funnel-shaped diversion element 13 is integrated into the packet of seal elements 15–17 and longitudinal bore 24 of probe housing 20 in such a way that gas permeability between diversion element 13 and the inner wall of the longitudinal bore of probe housing 20 is ensured, and that a small gap 26 remains open toward measured-gas sensor end II between sensing element 25 and diversion element 13.

The upper wide opening of funnel-shaped diversion element 13 is welded, by way of a sealed full-circumference laser weld 22, to inner protective sleeve 12 and to outer protective sleeve 11.

The effectiveness of funnel-shaped diversion element 13 lies in the fact that the hydrocarbons or water vapor diffusing from exhaust-gas side II through the lower dense powder packing 16 encounter the lower end surface of funnel-shaped diversion element 13 and there can for the most part escape into the atmosphere through gap 26 and through a gap remaining between inner protective sleeve 12 and the outer wall of probe housing 20.

The coarsely porous powder packing, which is placed in front of the end face of funnel-shaped diversion element 13 and is made, for example, of steatite that has been presintered at temperatures of about 750° C., improves the effectiveness of funnel-shaped diversion element 13 if care is taken that the diffusion resistance of coarsely porous powder packing 17 is much less by comparison with the connection-side upper dense powder packing 15 and the measured-gas-side dense powder packing 16.

The same effect is alternatively achieved by way of a ceramic disk (not depicted) which replaces coarsely porous powder packing 17 and is equipped at the end with radially extending ventilation grooves or transverse holes.

It should also be noted that inner protective sleeve 12 is connected, at its end facing toward exhaust-gas side II, to probe housing 20 via a caulked joint 28.

Further structural and functional features of the seal arrangement according to the present invention, and of the gas sensor equipped therewith, may be the same as in the gas sensor described in German Patent No. 195 32 090.

What is claimed is:

1. A seal arrangement for a sensing element of a gas sensor, the sensor including a metallic probe housing having an inner wall and a longitudinal bore, the seal arrangement comprising:
   a packet composed of a plurality of seal elements, the seal elements being packed one on top of another, the seal elements immobilizing the sensing element in the longitudinal bore of the probe housing; and
   a funnel-shaped diversion element lying in an axial direction of the sensor, the diversion element being integrated into the seal elements so as to ensure a gas permeability via a space between the diversion element and the inner wall of the probe housing, a small gap remaining open between the sensing element and the diversion element toward a measured-gas end of the sensor.

2. The seal arrangement according to claim 1, wherein the gas sensor is an oxygen sensor for determining an oxygen content in an exhaust gas of an internal combustion engine.

3. The seal arrangement according to claim 1, further comprising:
   an inner protective sleeve and an outer protective sleeve surrounding the sensing element toward a connection side; and
   a sealed full-circumference weld bead joining the diversion element, at a wide opening facing toward the connection side, to the inner and the outer protective sleeves.

4. The seal arrangement according to claim 3, wherein the inner and the outer protective sleeves and the diversion element are composed of a metal, and the weld bead is laser welded.

5. The seal arrangement according to claim 1, wherein the diversion element is shaped by deep-drawing.

6. The seal arrangement according to claim 1, wherein at least one of the seal elements includes a coarsely porous powder packing preceding an outer, measured-gas-side end face of the diversion element.

7. The seal arrangement according to claim 6, wherein the packing is composed of a presintered steatite.

8. The seal arrangement according to claim 6, wherein the seal elements further include a first dense powder packing, situated in an interior region of the diversion element, and a second dense powder packing, situated in an exterior region of the diversion element, the first and second dense powder packings having a diffusion resistance, the coarsely porous powder packing being packed between the first and second dense powder packings, the coarsely porous powder packing having a diffusion resistance substantially less than that of the first and second dense powder packings.

9. The seal arrangement according to claim 6, further comprising a ceramic disk having at least one of transverse holes and radially extending ventilation grooves opening toward the end face.

10. The seal arrangement according to claim 1, wherein the packet of seal elements lies between a connection-side insulating block and a measured-gasside insulating block.

11. The seal arrangement according to claim 10, further comprising an inner protective sleeve axially closing off the connection-side insulating block.

* * * * *